(12) United States Patent
Senda et al.

(10) Patent No.: US 10,846,849 B2
(45) Date of Patent: Nov. 24, 2020

(54) METHOD FOR ANALYZING STATE OF CELLS IN SPHEROID

(71) Applicant: Hitachi High-Tech Corporation, Tokyo (JP)

(72) Inventors: Naoko Senda, Tokyo (JP); Toshinari Sakurai, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 94 days.

(21) Appl. No.: 16/306,615

(22) PCT Filed: Jun. 16, 2016

(86) PCT No.: PCT/JP2016/067970
§ 371 (c)(1),
(2) Date: Dec. 3, 2018

(87) PCT Pub. No.: WO2017/216930
PCT Pub. Date: Dec. 21, 2017

(65) Prior Publication Data
US 2019/0244349 A1   Aug. 8, 2019

(51) Int. Cl.
*G06T 7/00* (2017.01)
*C12M 1/34* (2006.01)
(Continued)

(52) U.S. Cl.
CPC ............ *G06T 7/0012* (2013.01); *C12M 1/34* (2013.01); *C12Q 1/02* (2013.01); *G01N 21/27* (2013.01);
(Continued)

(58) Field of Classification Search
None
See application file for complete search history.

(56) References Cited

U.S. PATENT DOCUMENTS

2009/0079993 A1   3/2009   Yatagai et al.
2014/0064594 A1*  3/2014   Sugiyama ............ G02B 21/14
                                             382/133
(Continued)

FOREIGN PATENT DOCUMENTS

JP   11-230897       8/1999
JP   2003-57170 A    2/2003
(Continued)

OTHER PUBLICATIONS

Japanese-language Office Action issued in Japanese Application No. 2018-523123 dated Mar. 17, 2020 with English translation (12 pages).
(Continued)

*Primary Examiner* — Delomia L Gilliard
(74) *Attorney, Agent, or Firm* — Crowell & Moring LLP

(57) ABSTRACT

The present invention provides a method and an apparatus for analyzing a cell state, cell death in particular, in an interior of a spheroid non-invasively and quantitatively when the spheroid is cultured. More specifically, the present invention provides a method and an apparatus for analyzing a cell state by implementing optical imaging of a spheroid by using an optical instrument characterized by a high resolution and analyzing the internal structure of the spheroid.

10 Claims, 8 Drawing Sheets

(51) Int. Cl.
  *C12Q 1/02* (2006.01)
  *G01N 21/27* (2006.01)
  *G06K 9/00* (2006.01)
  *G06T 5/00* (2006.01)
(52) U.S. Cl.
  CPC ....... *G06K 9/0014* (2013.01); *G06K 9/00147* (2013.01); *G06T 5/009* (2013.01); *G06T 2207/10101* (2013.01); *G06T 2207/30024* (2013.01)

(56) References Cited

U.S. PATENT DOCUMENTS

| | | | |
|---|---|---|---|
| 2014/0065639 A1 | 3/2014 | Kobayashi | |
| 2015/0131889 A1 | 5/2015 | Aragaki | |
| 2016/0349240 A1* | 12/2016 | Fujimoto | ........... G01N 33/5008 |
| 2017/0159004 A1* | 6/2017 | Senda | .................... C12M 41/36 |
| 2017/0358081 A1 | 12/2017 | Tsumura | |

FOREIGN PATENT DOCUMENTS

| | | |
|---|---|---|
| JP | 2008-220779 A | 9/2008 |
| JP | 2012-61337 A | 3/2012 |
| JP | 2012-202761 A | 10/2012 |
| JP | 2013-27368 A | 2/2013 |
| JP | 2014-29287 A | 2/2014 |
| JP | 2014-66702 A | 4/2014 |
| JP | 2015-31812 A | 2/2015 |
| JP | 2015-181348 A | 10/2015 |
| JP | 2015-230168 A | 12/2015 |
| JP | 2016-21915 A | 2/2016 |
| WO | WO 2007/060973 A1 | 5/2007 |
| WO | WO 2014/021175 A1 | 2/2014 |
| WO | WO 2015/004762 A1 | 1/2015 |
| WO | WO 2015/141059 A1 | 9/2015 |
| WO | WO 2016/009789 A1 | 1/2016 |
| WO | WO 2015/145872 A1 | 10/2016 |

OTHER PUBLICATIONS

Extended European Search Report issued in European Application No. 16905485.5 dated Mar. 3, 2020 (11 pages).

International Search Report (PCT/ISA/210) issued in PCT Application No. PCT/JP2016/067970 dated Sep. 13, 2016 with English translation (five (5) pages).

Japanese-language Written Opinion (PCT/ISA/237) issued in PCT Application No. PCT/JP2016/067970 dated Sep. 13, 2016 (five (5) pages).

* cited by examiner

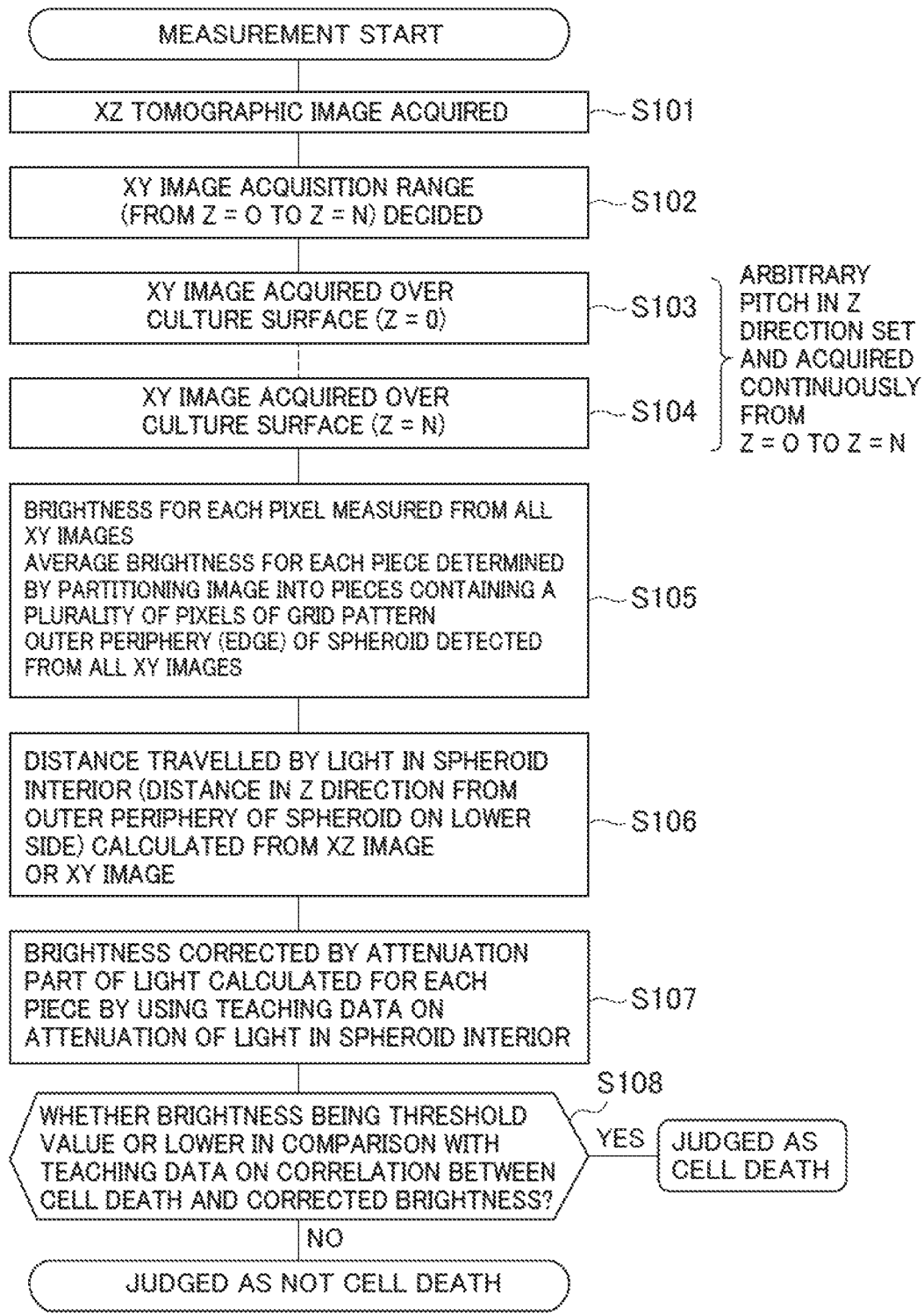

FIG. 2

| STATE OF CELLS | (S201) SEEDING | (S202) AGGLOMERATION | (S203) PROLIFERATION | (S204) INTERNAL NECROSIS | (S205) COLLAPSE |
|---|---|---|---|---|---|
| | ISOLATED STEM CELLS FLOATING IN CULTURE MEDIUM | STEM CELLS AGGLOMERATING AND SOME ADHERING TO CULTURE BOTTOM SURFACE | STEM CELLS PROLIFERATING AND FORMING SPHEROID | SOME OF CELLS IN SPHEROID INTERIOR BEING TO NECROSIS | CELLS DISSOCIATING AND SPHEROID COLLAPSING |
| IMAGE OF CULTURE SURFACE VIEWED LATERALLY | 202 / 201 | | | | |

IMAGE OF SPHEROID    OCT:xy IMAGES OF OCT

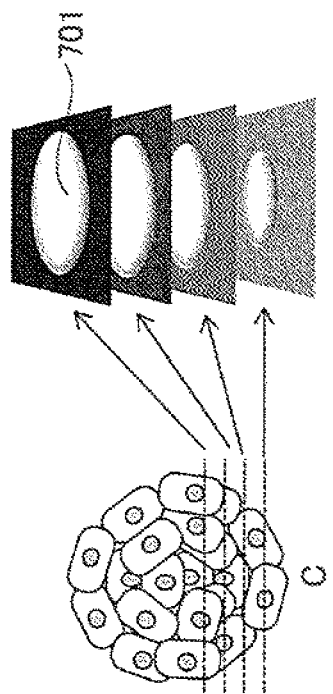
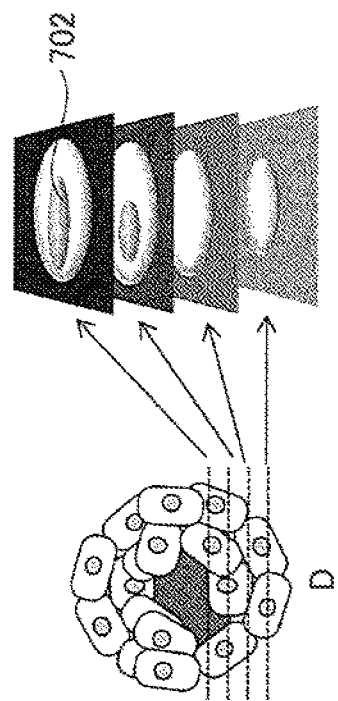
FIG. 7

METHOD FOR ANALYZING STATE OF CELLS IN SPHEROID

TECHNICAL FIELD

The present invention relates to a method and an apparatus for analyzing a cell state in a spheroid interior. Further, the present invention relates to a cell culture apparatus for manufacturing a spheroid.

BACKGROUND ART

Regenerative medicine is a medical treatment of recovering an original function by transplanting cells or a tissue created from stem cells into a tissue damaged by injury or disease, and is drawing attention in recent years. In the regenerative medicine, it has been known that a method of transplanting a biomimetic three-dimensional tissue has a higher survival rate to an affected part and a higher healing effect than a remedial method of injecting a suspension of discrete cells, and cell sheets for regenerating a cuticle and a cartilage are commercialized. Further, a spheroid that is a spherical agglomerate of a plurality of cells also draws attention as one form of three-dimensional tissues and research for practically using a cartilaginous spheroid or the like is promoted.

In a spheroid, it is known that cell death such as necrosis occurs mainly from a center part because nutrition and oxygen in a culture medium hardly reaches the cells in the center part during a culture process. The cell death here indicates necrosis (local death) and apoptosis (natural death). In necrosis, cells expand, cytoplasm changes, and cell membranes rupture. In apoptosis, cells shrink and are phagocytosed by immunocytes. However, the external form of a spheroid does not change. Meanwhile, a spheroid in the interior of which cell death occurs has a small number of living cells and an undesirable substance may possibly be released from the dead cells and hence such a spheroid is considered to be not suitable for transplantation.

The presence or absence of such a cell death region in a spheroid interior is thought to largely influence the quality of the spheroid. A spheroid, however, has heretofore been used mainly for drug development and cell death in a spheroid interior has not been a serious problem. Further, as an evaluation method of a spheroid, an invasive method of measuring the oxygen activity of living cells by using a pigment for living cell number measurement has been used. Even an invasive method has been acceptable in the case of a spheroid for drug development. On the other hand, in order to measure continuously and decide transplantation timing while a spheroid for transplantation is cultured, a non-invasive evaluation technology for a spheroid conforming to quality evaluation items is needed. Evaluation of a spheroid is currently verified by observation using a phase-contrast microscope, tissue staining, or the like. Although the cell observation using a phase-contrast microscope is non-invasive, it is impossible to measure the three-dimensional shape of a spheroid and evaluate cell death that occurs in the interior of a spheroid by the phase-contrast microscope. Further, although cell death can be evaluated by tissue staining, the tissue staining is an invasive method of fixing and embedding a spheroid, requires time for evaluation during culture and judgment of the result, and moreover cannot evaluate a spheroid itself for transplantation; and the evaluated spheroid can no longer be used for transplantation.

For the above reason, development of a technology that can non-invasively evaluate cell death in a spheroid interior is required. It can be said that the establishment of a non-invasive measurement technology of a three-dimensional shape of a spheroid and cell death in the interior thereof, which solves the above problems, contributes to the improvement of the quality of a regenerating tissue for transplantation by being able to directly evaluate the cell state of a spheroid for transplantation.

Non-invasive cell evaluation methods have heretofore been reported in some literatures. For example, Patent Literature 1 describes a method of: obtaining a three-dimensional image of a skin interior by using reflected light; and identifying a site of a melanin pigment by a part of a relatively high brightness. Further, Patent Literature 2 describes a method of: obtaining a three-dimensional image of a cell sheet by using an optical coherence tomograph; and deciding a defective part of cells and the thickness of the cell sheet by brightness. Patent Literature 3 describes a method of: obtaining a three-dimensional image of a cell sheet by using reflected light; and determining the degrees of stratification and differentiation of the cell sheet from the distribution of nuclei in the obtained cell sheet interior. Patent Literature 4 describes a method of: obtaining cells of monolayer culture by using a microscope and determining living cells from necrotic cells.

CITATION LIST

Patent Literature

Patent Literature 1: JP Patent Publication No. 2003-057170 A
Patent Literature 2: WO 2015/004762 A
Patent Literature 3: JP Patent Publication No. No. 2016-021915 A
Patent Literature 4: JP Patent Publication No. No. 2014-029287 A

SUMMARY OF INVENTION

Technical Problem

In any of the above patent literatures, a non-invasive means such as three-dimensional measurement or microscopic observation by reflected light is used with the aim of detecting a specific site in a living tissue or cells. The surface of the living tissue or the cells targeted by the prior art documents, however, is planar and the living tissue or the cells does/do not have such a shape close to a sphere such as a spheroid. In the case of reflected light measurement, the strength of signal light from a measurement object reduces by the influence of scattering and the like while the signal light advances in the measurement object, when the surface of the measurement object is flat, correction is unnecessary for comparing brightness in an identical planar image during the analysis of a tomographic image parallel with the surface. When cell death existing in the interior of such a tissue close to a sphere such as a spheroid is detected by reflected light, however, a distance travelled by light from a spheroid surface to a measurement point varies for each of the measurement points even in an identical planar image, hence the brightness cannot simply be compared, and the cell death cannot be judged by a conventional method of not using correction. In the present invention therefore, a problem is to analyze cell death in a spheroid interior.

Solution to Problem

As a result of studying earnestly in order to solve the above problems, the present inventors have found that a cell state in a spheroid interior can be analyzed non-invasively and quantitatively by implementing optical imaging of a spheroid and correcting the brightness of an acquired image on the basis of a three-dimensional shape of the spheroid and/or a distance from a light irradiation position to a measurement position, and have completed the present invention.

Three-dimensional measurement by reflected light may be effective as a method and an apparatus for analyzing a cell state in a spheroid interior non-invasively. Since reflected light weakens more by the change of cytoplasm and the disruption of cell membranes in a region where cell death occurs than in normal living cells, a region of brightness below a certain level can be judged as cell death by analyzing the brightness of an image acquired through reflected light imaging.

Specifically, in an embodiment, the present invention provides a cell analysis method of analyzing a cell state in the interior of a spheroid, including:

a step of irradiating the spheroid with light;

a step of acquiring a plurality of spheroid cross-sectional images having different distances from a light irradiation position; and a step of correcting brightness of the images in consideration of signal strength attenuation.

In another embodiment, the present invention provides a cell analysis apparatus for analyzing a cell state in the interior of a spheroid, including:

a light source, a light condensation optical system configured to irradiate cells on a culture surface with light from the light source, and a detection optical system configured to detect light from the cells; and an analysis unit configured to analyze an image based on information acquired from the detection optical system, and wherein the analysis unit has:

an image acquisition unit configured to acquire a plurality of cross-sectional images having different distances from the culture surface in the vertical direction;

a brightness measurement unit configured to measure brightness of the plurality of cross-sectional images; and a state analysis unit configured to correct the brightness in consideration of signal strength attenuation and analyze a cell state in the spheroid interior.

In still another embodiment, the present invention provides a cell culture apparatus having a culture unit configured to culture a spheroid, an analysis unit configured to analyze a cell state in the interior of the spheroid by using light, and a control unit configured to control culture and analysis of the spheroid, wherein (1) the analysis unit has:

a light source, a light condensation optical system configured to irradiate cells on a culture surface with light from the light source, a detection optical system configured to detect light from the cells; and an image analysis unit configured to analyze an image based on information acquired from the detection optical system, and the image analysis unit has:

an image acquisition unit configured to acquire a plurality of cross-sectional images having different distances from the culture surface in the vertical direction;

a brightness measurement unit configured to measure brightness of the plurality of cross-sectional images; and a state analysis unit configured to analyze a cell state in the spheroid interior on the basis of the brightness, and (2) the control unit controls at least one of supply of a cell solution, supply of a culture medium, disposal of a culture medium, culture of cells, irradiation of light, detection of light, acquisition of an image, measurement of brightness, and analysis of a cell state.

Advantageous Effects Of Invention

The present invention provides a method and an apparatus for analyzing a cell state in the interior of a spheroid and a cell culture apparatus for culturing the spheroid on the basis of the method and the apparatus. The method and the apparatus according to the present invention can analyze a cell state (namely, the presence or absence of cell death) in the interior non-invasively and quantitatively when the spheroid is cultured, and are useful for manufacturing a spheroid, in particular a spheroid used for regenerative medicine such as transplantation.

BRIEF DESCRIPTION OF DRAWINGS

FIG. 1 is a schematic diagram showing an analysis flow of a cell state in a spheroid interior.

FIG. 2 is a conceptual diagram showing stages from manufacturing to collapse of a spheroid.

FIG. 7 shows conceptual images of the presence or absence of cell death in spheroid interiors and OCT images.

DESCRIPTION OF EMBODIMENTS

Figure 3:
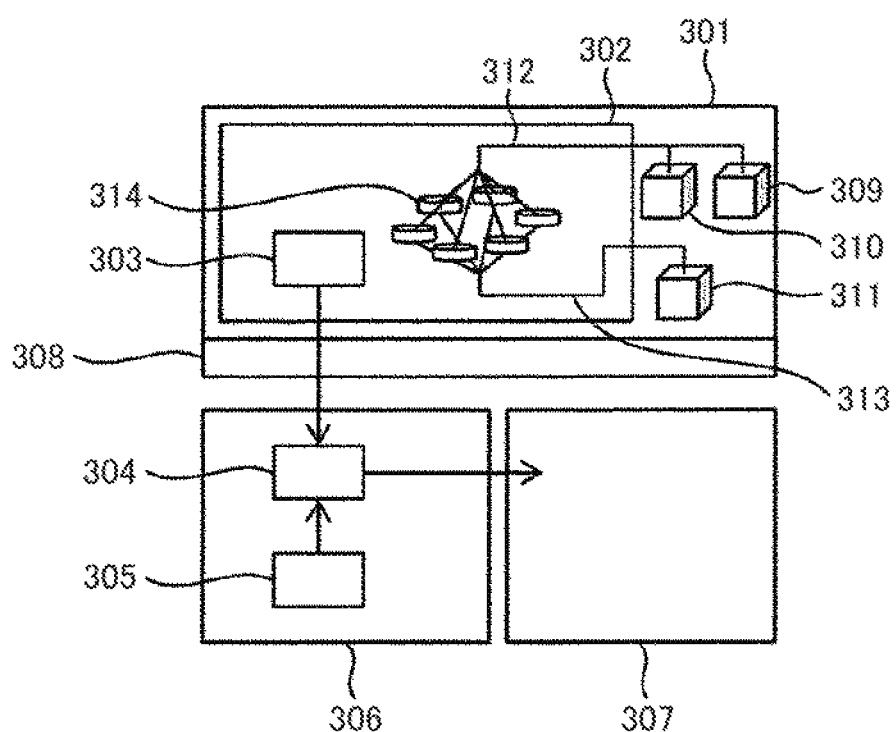
FIG. 3 is a block diagram showing an example of an automated cell culture apparatus incorporating an OCT.

Embodiments of the present invention are explained in detail in reference to the drawings. The present invention, however, is not interpreted as being limited to the contents described in the embodiments shown below. A person skilled in the art can easily understand that a specific configuration can be modified within a range not departing from the sprit or the meaning of the present invention.

Further, a position, a size, a shape, a range, and the like in each of the configurations shown in the drawings and others may not represent an actual position, size, shape, range, and the like in some cases in order to facilitate the understanding of the invention. The present invention therefor is not necessarily limited to the position, size, shape, range, and the like disclosed in the drawings and others.

The present invention relates to a method and an apparatus for analyzing a cell state in a spheroid interior. A spheroid refers to a three-dimensional cell aggregate formed by aggregating and agglomerating cells. A spheroid including, but not limited to, a spheroid comprising stem cells, chondrocytes, liver cells, corneal cells, epidermal cells, cardiomyocytes, neurocytes, and progenitor cells of any of them can be used in the present invention. Further, an origin of cells is also not particularly limited and for example cells of an animal, desirably a mammal, and specifically cells derived from a primate (a human, a monkey, a chimpanzee, a gorilla, and the like), an experimental animal (a mouse, a rat, and the like), a domestic animal (a cow, a pig, a rabbit, and the like), or a pet animal (a dog, a cat, and the like) can be adopted.

Stages from manufacturing to collapse of a spheroid are shown in FIG. 2. FIG. 2 represents images of observing the structure of cells from a lateral direction when a culture surface 201 is regarded as extending in a depth direction of the figure. Stem cells are used here as an example. A spheroid grows to a three-dimensional tissue through the following stages.

(S201): Cells are seeded. In this stage, isolated stem cells 202 are in the state of floating in a culture medium.

(S202): The stem cells 202 agglomerate and some of them adhere to a culture surface 201. Culture equipment having a flat bottom surface and a high cell adhesiveness may be used in the case of plate culture but, in the case of spheroid culture, cells can be agglomerated by: using culture equipment having a round bottom as shown in the figure; applying minute unevenness to a culture surface; or lowering cell adhesiveness through surface treatment of a culture surface.

(S203): The agglomerated cells proliferate and form a spheroid. At the time when the agglomerated cells are cultured into an appropriate spheroid, the spheroid is taken out from a culture vessel and transplanted into an affected part.

(S204): In a spheroid, it is known that cell death such as necrosis occurs mainly from a center part because nutrition and oxygen in a culture medium hardly reaches the cells in the center part during a culture process. The cell death here indicates necrosis (local death) and apoptosis (natural death). In necrosis, cells expand, cytoplasm changes, and cell membranes rupture. In apoptosis, cells shrink and are phagocytosed by immunocytes. However, the external form of a spheroid does not change. Meanwhile, a spheroid in the interior of which cell death occurs has a small number of living cells and an undesirable substance may possibly be released from the dead cells.

(S205): Finally, the cells dissociates and the spheroid collapses.

In order to assure the quality of a spheroid, it is necessary to analyze a cell state in the interior of the spheroid, namely the presence or absence of cell death (necrosis and apoptosis) during the culture and before transplantation. Desirably, a spheroid in the vicinity of a culture surface (spheroid formed by agglomerating cells in the vicinity of a culture surface) is analyzed.

According to the present invention, a cell state (namely the presence or absence of cell death) in a spheroid interior may be analyzed by: optically imaging a spheroid by using an optical instrument characterized by a high resolution; and analyzing an acquired image. A cell state in a spheroid interior may be analyzed by: imaging a three-dimensional structure of a spheroid with reflected-light at a cell-level resolution; and, from a plurality of cross-sectional images, measuring a three-dimensional shape of the spheroid, and tomographic images the brightness of which is corrected at points in accordance with distances travelled by light in a sample on the basis of the three-dimensional shape. Since reflected light weakens more in a region where cell death occurs by the change of cytoplasm and the disruption of cell membranes than in normal living cells, a region where the brightness is not higher than a certain level can be judged as cell death by analyzing the brightness of images acquired through reflected-light imaging. In the case of reflected light measurement, the strength of signal light from a measurement object attenuates by the influence of scattering or the like while the signal light advances through the measurement object. When cell death existing in the interior of a tissue close to a spherical shape such as a spheroid is detected with reflected light, the above correction is applied because the distances travelled by light from a spheroid surface to measurement points may vary depending on the measurement points even in an identical planar image and hence the brightness cannot be simply compared.

An embodiment of the present invention is a method of analyzing a cell state in a spheroid interior when a spheroid is cultured. In this method, firstly a step of irradiating a spheroid with light during culture or after the end of culture is implemented. For the irradiation of light, a light source, a light condensation optical system configured to irradiate cells of a spheroid with light from the light source, a detection optical system configured to detect light from the cells, and a detector configured to detect light from the detection optical system may be used. For example, a light source, a light condensation optical system, and a detection optical system may be: any optical instruments as long as the optical instruments have high resolutions to three-dimension; and desirably non-invasive (non-destructive and non-staining) optical instruments. Specifically, for example the optical instruments may be configured as an OCT (Optical Coherence Tomograph), a reflection confocal microscope, a multi-photon excitation microscope, or the like.

When an OCT is used as an optical system, the case is based on the principle of dividing the light of a light source into signal light and reference light, irradiating cells with the signal light, and detecting composite light created by combining the signal light reflected from the cells and the reference light. In the OCT, signal light may be reflected in the manner of overlapping from various depths in cells, the component interfering with reference light is limited to a signal light component from positions of specific depths, and hence measurement of a high resolution in the Z direction comes to be possible unlike an optical microscope.

In the case of an OCT having a high spatial resolution of about 10 microns or lower, light or dark of each cell unit in a spheroid interior can be imaged from an acquired image. Brightness lowers in a region where cell death occurs in comparison with a normal cell part and hence the presence or absence and the volume of the cell death can be analyzed. Whether or not the culture process of a spheroid is favorable and the spheroid is transplantable can be judged by the information. Further, the analysis method of a cell state can be automated by an existing image processing technology. It is also possible to incorporate an OCT into an automated cell culture apparatus and measure a spheroid cultured in a culture vessel in the automated cell culture apparatus with the OCT.

A plurality of spheroid cross-sectional images having different distances from a light irradiation position (for example, distances from a culture surface in the vertical direction) may be acquired on the basis of a signal from the detector. Then a three-dimensional shape of a spheroid, and tomographic images the brightness of which is corrected on the basis of the three-dimensional shape may be measured from the plurality of cross-sectional images and brightness information after the correction may be acquired at each point. Specifically, brightness in a tomographic image may be influenced by the three-dimensional shape of a spheroid and/or a distance from a light irradiation position to a measurement position; and the brightness lowers and a signal strength attenuates as the degree of overlapping cells in the three-dimensional shape increases and the distance from the irradiation position increases. In the present invention therefore, a problem intrinsic to a spheroid can be solved by correcting brightness in consideration with such signal strength attenuation. Since the signal strength attenuation varies in accordance with a type of cells used, a optical system device used, a sample composition, and others, it may be possible to correct brightness from data of signal strength attenuation related to a specific cell state in a spheroid interior that has been learned beforehand. Such correction may be applied either automatically in an analysis unit or manually by an operator.

In the case of analyzing brightness, it is desirable to: partition a spheroid cross-sectional image into pieces containing a plurality of pixels of a grid pattern; and determine an average brightness for each of the pieces. Unevenness of brightness caused by noises, local refractive index difference in cells, and the like exists between pixels in a cross-sectional image. More accurate and quantitative image evaluation can be implemented by partitioning the image into pieces containing a plurality of pixels of a grid pattern and acquiring an average value of brightness for each piece unit.

Reflected light weakens more in a part where cell death occurs in a spheroid interior by the change of cytoplasm and the disruption of cell membranes than in normal living cells. As a result, it is possible to estimate that a cell in a cell death state exists at a part when the brightness of an image acquired by reflected light imaging is analyzed and resultantly is lower than a certain value. On the other hand, when brightness is higher than a certain value, it is possible to estimate that a cell in a cell death state does not exist at the part. Further, it is also possible to quantitatively analyze how many cells of a cell death state exist from a value of brightness. Since the value of brightness related to a cell state varies depending on a type of cells used, a optical system device used, a sample composition, and others, it is possible to analyze a cell state in a spheroid interior from a specific cell state in the spheroid interior, namely from brightness data related to the presence or absence of cell death, which has been learned beforehand.

Further, according to an embodiment of the present invention, when the external shape or the volume of a spheroid does not change after the aforementioned steps are applied, a step of irradiating the spheroid with light again and acquiring a second cross-sectional image of the spheroid may be applied further. In this step, it is desirable to implement the correction of matching the position of the spheroid when brightness is measured in the aforementioned steps with the position of the spheroid in the second cross-sectional image. By comparing the brightness of the acquired second image with the brightness of the image acquired through the aforementioned steps at the identical or equivalent positions, it is possible to analyze or monitor a cell state in the spheroid interior over time. In this case, such signal strength attenuation as described above is not required to be taken into consideration and analysis can be implemented more conveniently.

Furthermore, another embodiment of the present invention is a cell analysis apparatus for analyzing a cell state in the interior of a spheroid non-invasively and optically. The apparatus has a light source, a light condensation optical system configured to irradiate cells on a culture surface with light from the light source, a detection optical system configured to detect light from the cells, and an analysis unit configured to analyze an image based on information acquired from the detection optical system. The light source, the light condensation optical system, and the detection optical system may be optical instruments having high resolutions to three dimensions as stated above, or preferably non-invasive (non-destructive and nonstaining) optical instruments. In a preferable embodiment, the light source, the light condensation optical system, and the detection optical system may be configured as an optical coherence tomograph (OCT).

Further, the analysis unit has an image acquisition unit configured to acquire a plurality of cross-sectional images having different distances from a culture surface in the vertical direction, a brightness measurement unit configured to measure the brightness of the plurality of cross-sectional images, and a state analysis unit configured to correct the brightness in consideration of signal strength attenuation and analyze a cell state in a spheroid interior. The analysis unit can be configured so as to analyze a cell state (for example, the presence or absence of cell death) in a spheroid interior from a three-dimensional shape of a spheroid and the brightness of tomographic images, which is corrected on the basis of the three-dimensional shape. The analysis unit may further have a measurement unit configured to measure the external shape of a spheroid and this makes it possible to measure the external shape and/or the volume of the spheroid and assist the correction of brightness considering signal strength attenuation and the analysis of a cell state in a spheroid interior.

Furthermore, a cell analysis apparatus according to the present invention may have an output device or may be connected to an external output device. The output device can be any output device publicly known in the art, and may include an image and/or data display device, an alarm system, and a printer, for example. In this case, an analysis unit may also be configured so as to display, on a display device, images before and after correction, an image showing a part judged as cell death in images after correction, and a ratio of the volume of a cell death part to the volume of a spheroid. Further, an analysis unit may also be configured so as to implement at least one of: raise of an alarm from an alarm system on the basis of analysis data; and output of a signal based on analysis data to a cell culture apparatus or another external device.

A cell analysis apparatus according to the present invention desirably further has a memory unit configured to store signal strength attenuation data and/or brightness data related to a specific cell state in the interior of a spheroid. Since a value of brightness related to signal strength attenuation and a specific cell state varies depending a type of cells used, a optical system device used, a sample composition, and others as stated earlier, it is possible to correct brightness quickly and easily by storing the data of signal strength attenuation related to a specific cell state in the spheroid interior in a memory unit and comparing with the stored data. Further, by storing brightness data of a specific cell state, namely the presence or absence of cell death, in the spheroid interior in the memory unit, it is possible to analyze a cell state in the spheroid interior quickly and easily by comparing with the stored data.

Still another embodiment of the present invention is a cell culture apparatus for culturing a spheroid and has (1) a culture unit configured to culture a spheroid, (2) an analysis unit configured to analyze a cell state in the interior of the spheroid by using light, and (3) a control unit configured to control the culture and analysis of the spheroid.

The culture unit in the cell culture apparatus may not be particularly limited as long as cells can be cultured and a spheroid can be formed in the culture unit. Those skilled in the art can configure an appropriate culture unit in accordance with the type of objective cells of interest and the intended use of the spheroid. In an embodiment, a culture unit can be a unit having a thermostatic chamber, a culture vessel to be arranged in the thermostatic chamber, which is configured to culture a spheroid, a cell bottle being connected to the culture vessel, which is configured to supply a cell solution, a culture medium bottle being connected to the culture vessel, which is configured to supply a culture medium, and a waste fluid bottle being connected to the culture vessel, which is configured to store a culture medium discarded from the culture vessel.

The analysis unit in the cell culture apparatus may have a light source, a light condensation optical system configured to irradiate cells on a culture surface with light from the light source, a detection optical system configured to detect light from the cells, and an image analysis unit configured to analyze an image based on information acquired from the detection optical system. The image analysis unit may have an image acquisition unit configured to acquire a plurality of cross-sectional images having different distances from the culture surface in the vertical direction, a brightness measurement unit configured to measure brightness of the plurality of cross-sectional images, and a state analysis unit configured to analyze a cell state in a spheroid interior on the basis of the brightness. The image analysis unit may have the function of acquiring a plurality of cross-sectional images having different distances from the culture surface in the vertical direction on the basis of a signal from the detection optical system, and the function of measuring a three-dimensional shape of a spheroid, and tomographic images the brightness of which is corrected on the basis of the three-dimensional shape from the plurality of cross-sectional images and analyzing a cell state in a spheroid interior on the basis of the brightness of the images. Specifically, the state analysis unit corrects the brightness of cross-sectional images in consideration of signal strength attenuation and analyzes a cell state in a spheroid interior.

The control unit in the cell culture apparatus may control at least one of supply of a cell solution, supply of a culture medium, disposal of a culture medium, culture of cells, irradiation of light, detection of light, acquisition of an image, measurement of brightness, and analysis of a cell state. For example, the control unit is configured so as to control the culture of a spheroid in the culture unit on the basis of an output from the state analysis unit. As the control unit, any control means publicly known in the art, for example, a computer may be used.

A cell culture apparatus according to the present invention may further have an output device and the output device can implement at least one of display of measured information, raise of an alarm based on the measured information, output to an external device, and feedback to the control unit or an input unit. Here, the alarm includes both notifying abnormality and notifying normality.

The functions explained above may be configured by either hardware or software.

Yet another embodiment of the present invention is a cell state analysis apparatus which receives data from a cell culture apparatus (cell culture unit) configured to culture a spheroid and analyzes a cell state in the interior of the spheroid cultured in the cell culture apparatus. The cell culture apparatus and the cell state analysis apparatus may either be integrated or be connected by a network and be arranged at geometrically distant positions.

In this embodiment, a cell culture apparatus has a light source, a light condensation optical system configured to irradiate cells on a culture surface with light from the light source, a detection optical system configured to detect light from the cells, a detector configured to detect light from the detection optical system, and an output device. A processing apparatus constituting a cell state analysis apparatus has: the function of acquiring a plurality of cross-sectional images having different distances from a culture surface in the vertical direction on the basis of a signal from the detector sent from the output device of the cell culture apparatus; and the function of measuring a three-dimensional shape of a spheroid, and tomographic images the brightness of which is corrected on the basis of the three-dimensional shape from the plurality of cross-sectional images, and analyzing a cell state (for example, the presence or absence of cell death) in a spheroid interior on the basis of the brightness of the images. The information measured through the above process can be displayed on a display device, can be accumulated as data in a memory device, or can be transmitted to an external device as data through a network. Otherwise, at least a part of the cell culture apparatus can be configured so as to be controlled on the basis of the measured information.

The present invention is explained more specifically hereinbelow on the basis of examples; but is not limited to the examples.

EXAMPLE 1

In the present example, non-invasive three-dimensional measurement of a spheroid and analysis of a cell state in a spheroid interior in an automated cell culture apparatus are explained as an example.

FIG. 3 shows an example of an automated cell culture apparatus incorporating an OCT (Optical Coherence Tomograph). An automated cell culture apparatus 301 in FIG. 3 has a thermostatic chamber 302 configured to culture cells. An imaging unit 303 may be installed in the thermostatic chamber. A computer 306 including an analysis unit 304 and a memory unit 305, and an output device 307 may be installed outside the thermostatic chamber. The output device 307 may include an image display device configured to display various kinds of information to an operator, an alarm system to raise an alarm by voice, or a printer, for example. Further, the output device can transmit data to an external memory device and an information terminal through a network or the like. Otherwise, the output device can send an instruction to a control unit 308 through various interfaces. The automated cell culture apparatus may be controlled by the control unit 308. Cells may be cultured in a plurality of culture vessels 314 installed in the interior of the thermostatic chamber 302. A required cell solution passes through a medium flow path 312 and is supplied from a cell bottle 309. A culture medium passes through the medium flow path 312 and is supplied from a culture medium bottle 310 to the culture vessels 314. An unnecessary culture medium used for culture passes through a waste flow path 313 and is discarded to a waste fluid bottle 311.

The quality of a spheroid can be evaluated by measurement using the imaging unit 303 configured to acquire the spheroid image from the exterior of the culture vessels. In the present embodiment, an OCT (Optical Coherence Tomograph) is used for the imaging unit 303. The overall configuration of the part of implementing non-invasive three-dimensional measurement comprises the imaging unit 303 configured to acquire a spheroid image, the analysis unit 304 configured to analyze acquired images and analyze the state of cells in a spheroid interior, the memory unit 305 configured to store information necessary for analysis beforehand, and the output device (here, an image monitor is assumed) 307 configured to display the analysis result. The automated cell culture apparatus in FIG. 3 may have an amino acid analysis unit (not shown in the figure) including an amino acid analysis device. An old culture medium to be a waste fluid during culture medium exchange passes through the waste flow path 313 from the culture vessels 314 and is discarded to the waste fluid bottle 311 but a part of a culture supernatant passes through a flow path for culture supernatant analysis (not shown in the figure) branched from the waste flow path 313 and is transported to the amino acid analysis unit and an amino acid concentration in the supernatant can be analyzed.

A cell state may be analyzed by the analysis unit 304 and fed back to the control unit 308 in the automated cell culture apparatus for deciding culture end timing and evaluating the quality of a culture tissue. Otherwise, a cell state may be displayed on the output device 307 and an operator may judge the cell state, decide culture end timing, and evaluate the quality of a culture tissue. Further, an operator may input into an input unit (not shown in the figure) in order to operate the control unit 308 and the computer 306 in the automated cell culture apparatus as necessary. The input unit may also be configured so as to be able to input an instruction from a remote place through a network. In the present embodiment, as the method of implementing the analysis unit 304, the analysis unit 304 is configured as software operating on a general-purpose computer 306 but can also be configured by hardware.

In the embodiment in FIG. 3, an example of arranging in proximity to the automated cell culture apparatus 301 or integrating the computer 306, the control unit 308, and others is shown. The positions of the computer 306, the control unit 308, and others, however, are not limited to the case. In the present day when a wired or wireless network has developed, a case of connecting those units with a network through the output device 307 and arranging those units at remote places is also included in the range of the disclosure of the present invention.

More features of the present invention are explained below with specific examples. Here, an OCT is used as an imaging unit 303 in the example.

Figure 4:
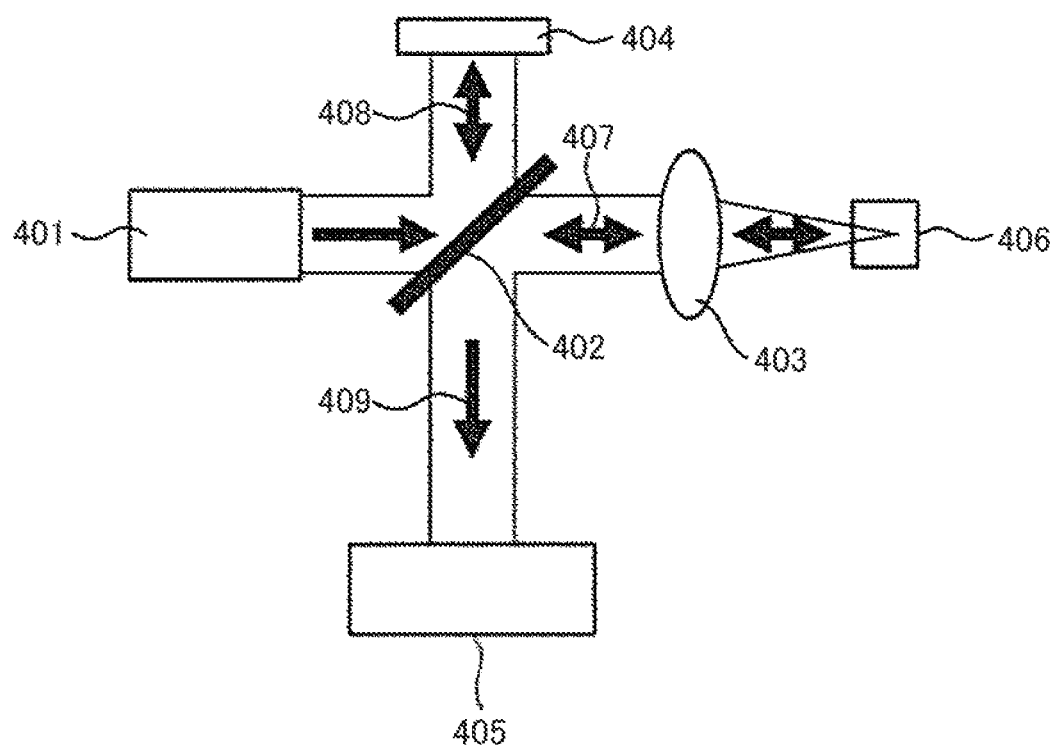
FIG. 4 is a configuration diagram showing a basic configuration example of an OCT.

A basic configuration example of an OCT (Optical Coherence Tomograph) that is an imaging unit 303 is shown in FIG. 4. The OCT comprises a light source 401, a beam splitter 402, an objective lens 403, a reference light mirror 404, and a detector 405. Light from the light source 401 is divided into signal light 407 and reference light 408 and cells 406 are irradiated with the signal light 407. Coherent light 409 generated by combining the signal light reflected from the cells and the reference light is detected by the detector 405. As a result, the structure of the cells is visualized. One kind of coherent light is generated in FIG. 4 but it is also possible to be configured so as to have an interference optical system of generating three or more kinds of coherent light having different phases from each other.

Figure 5:
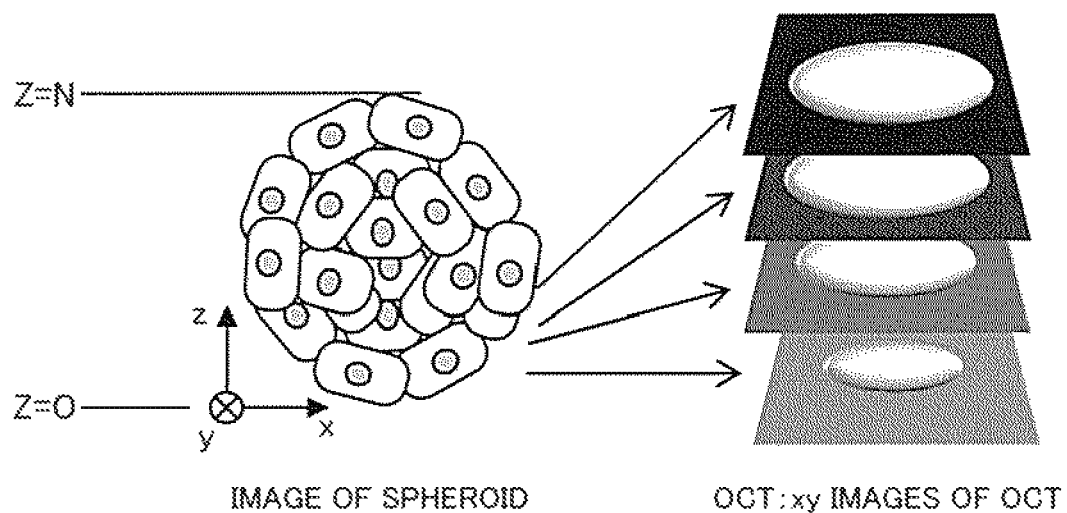
FIG. 5 is a conceptual image of measuring a spheroid.
Figure 6:
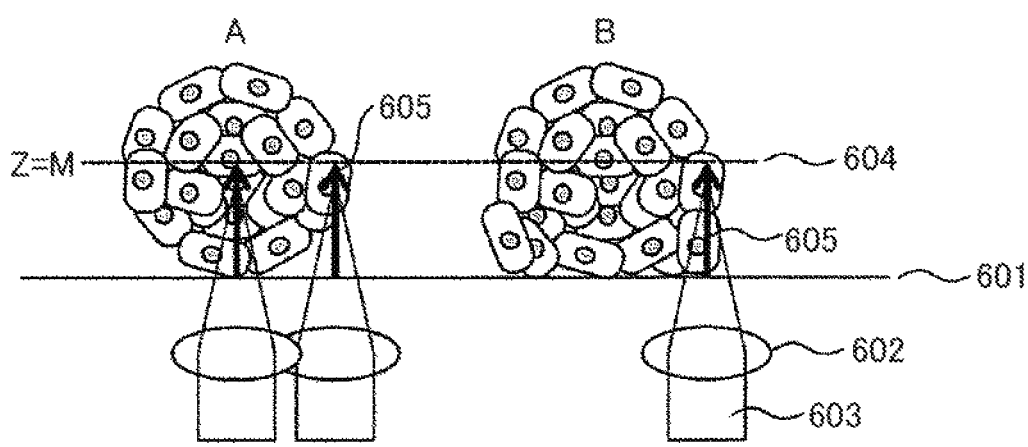
FIG. 6 is a conceptual image of a relationship between a three-dimensional shape of a spheroid and a distance travelled by light.

A schematic diagram of the flow of measuring a spheroid with an OCT and analyzing a cell state in a spheroid interior is shown in FIG. 1. A conceptual image of measuring a spheroid is shown in FIG. 5. A perspective view of a spheroid is imaged on the left side in FIG. 5. The x, y, and z axes are defined as shown in the figure. Images on xy planes located at different positions on the z axis acquired from the OCT are shown on the right side in FIG. 5. A conceptual image of a relationship between a three-dimensional shape of a spheroid and a distance travelled by light relating to (S106) in FIG. 1 is shown in FIG. 6. Conceptual images of the presence or absence of cell death in spheroid interiors and OCT images are shown in FIG. 7. Conceptual images of OCT images before and after correction relating to (S105) and (S107) in FIG. 1 are shown in FIG. 8.

The flow of measurement and analysis in FIG. 1 is explained mainly. Firstly, XZ tomographic images of a spheroid are acquired at an OCT imaging unit 303 installed in the interior of a thermostatic chamber 302 (S101). The orientations of X, Y, and Z are as shown in FIG. 5, an XY plane is a plane parallel with a culture surface, and the Z axis is the axis perpendicular to the culture surface. The thickness in the Z direction (Z=0 to N) of the spheroid may be clarified from the XZ tomographic images and hence is defined as an XY image acquisition range (S102). Successively, XY images are acquired from Z=0 to Z=N sequentially in XY visual fields (S103 to S104). On this occasion, analysis of a higher degree of accuracy can be obtained as the imaging intervals from Z=0 to Z=N reduce but the intervals can be appropriately set. As a desirable example, the intervals are set so as to be smaller than expected sizes of cells in the Z direction. In acquired XY images, living cells in the spheroid are imaged brightly and, if the region of cell death exists at a part of the spheroid, the region is imaged darkly. The spheroid has a shape close to a spherical shape and cells of the lower part of the surface do not necessarily adhere to the culture bottom surface, however, and hence, even in an XY image of a certain position in the Z direction, brightness of each point cannot be compared without correction. For example, even in the measurement of a spheroid A at Z=M as shown in FIG. 6, signal light attenuates at the center part of the spheroid because the distance travelled by light in the spheroid interior is large and apparent brightness reduces in comparison with an end part. Further, when the shape of a spheroid deviates from a spherical shape like B shown in FIG. 6, the distance travelled by light in the spheroid interior is large like the center part even at an end part of the spheroid and apparent brightness reduces in some cases. As a result, cell death in a spheroid interior can be determined as shown in FIG. 7 for the first time by correction that will be described later.

Figure 8:
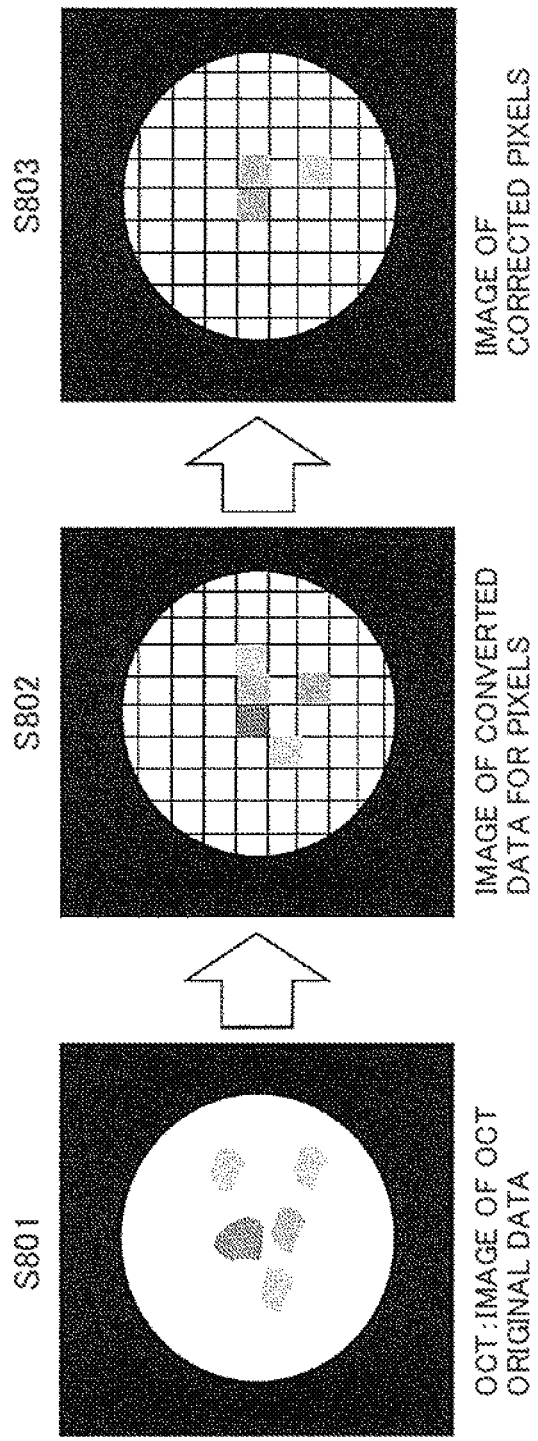
FIG. 8 shows conceptual images of OCT images before and after correction.

Since unevenness of brightness exists even in a relatively narrow region when each of pixels in an actual XY image is examined precisely, an image is partitioned into pieces containing a plurality of pixels of a grid pattern and an average brightness of each of the pieces is determined ((S105) in FIG. 1, (S801) to (S802) in FIG. 8). Further, the outer periphery (edge) of a spheroid is detected by using all the XY images ((S105) in FIG. 1). Then, a distance travelled by light in a spheroid interior (a distance from the outer periphery of the spheroid on the lower side in the Z direction) is calculated from XY images or XZ images for each piece ((S106), FIG. 6). Next, brightness corrected by the attenuation part of light is calculated for each piece by using correlation data of the attenuation of light in the spheroid interior, which are a part of teaching data stored in a memory unit 305 beforehand (S107, S803). The teaching data used here is considered to change also by the composition of a cell constituting a spheroid and hence it is desirable to measure the teaching data beforehand for each of the cells to be measured. Further, whether or not a piece causes cell death may be judged by comparing the brightness of each piece after the correction with the correlation data between cell death and brightness after correction that is a part of the teaching data stored in the memory unit 305 beforehand. Cells may be judged: to be cell death when brightness is a threshold value or lower; and to be normal living cells otherwise. It is desirable to select the teaching data used here by measuring correlation between brightness measurement by reflected light and cell death beforehand in combination with another method that can determine cell death such as tissue staining. The three-dimensional shape and the size of a spheroid, the presence or absence of cell death and the volume of a cell death region in a spheroid interior, and the like, which can be final analysis results, are displayed on a display unit as an output device 307. When the results are displayed in real time, the status of cells can be monitored. Furthermore, remote control is also possible by transmitting to an external device through a network. Otherwise, when the analysis results satisfy a specific condition, an alarm can be raised by a sound, an image, or the like.

As stated above, according to an embodiment of the present invention, a cell death part in a spheroid interior can be determined by analyzing a three-dimensional shape of a spheroid and tomographic images the brightness of which is corrected at each point in accordance with distances travelled by light in a sample on the basis of the three-dimensional shape. Further, information on a cell state of a spheroid can be notified to an operator by displaying the three-dimensional shape and the volume of the spheroid, and the presence or absence and the volume of a cell death region in the spheroid interior on a display device or storing them in a memory device.

In an automated cell culture apparatus explained in the example of the present invention, it is possible to: acquire three-dimensional information of cells non-invasively; and, on the basis of the information, feed back warnings or instructions to a device or an operator automatically.

In the present example, a function equivalent to a function configured by software can be implemented also by hardware. Such an embodiment is also included within the scope of the present invention.

EXAMPLE 2

In the present example, another example of non-invasive three-dimensional measurement of a spheroid and analysis of a cell state in a spheroid interior in an automated cell culture apparatus is explained.

The device configuration is similar to Example 1 and can be a device having the configuration shown in FIGS. 3 and 4 for example.

Figure 9:
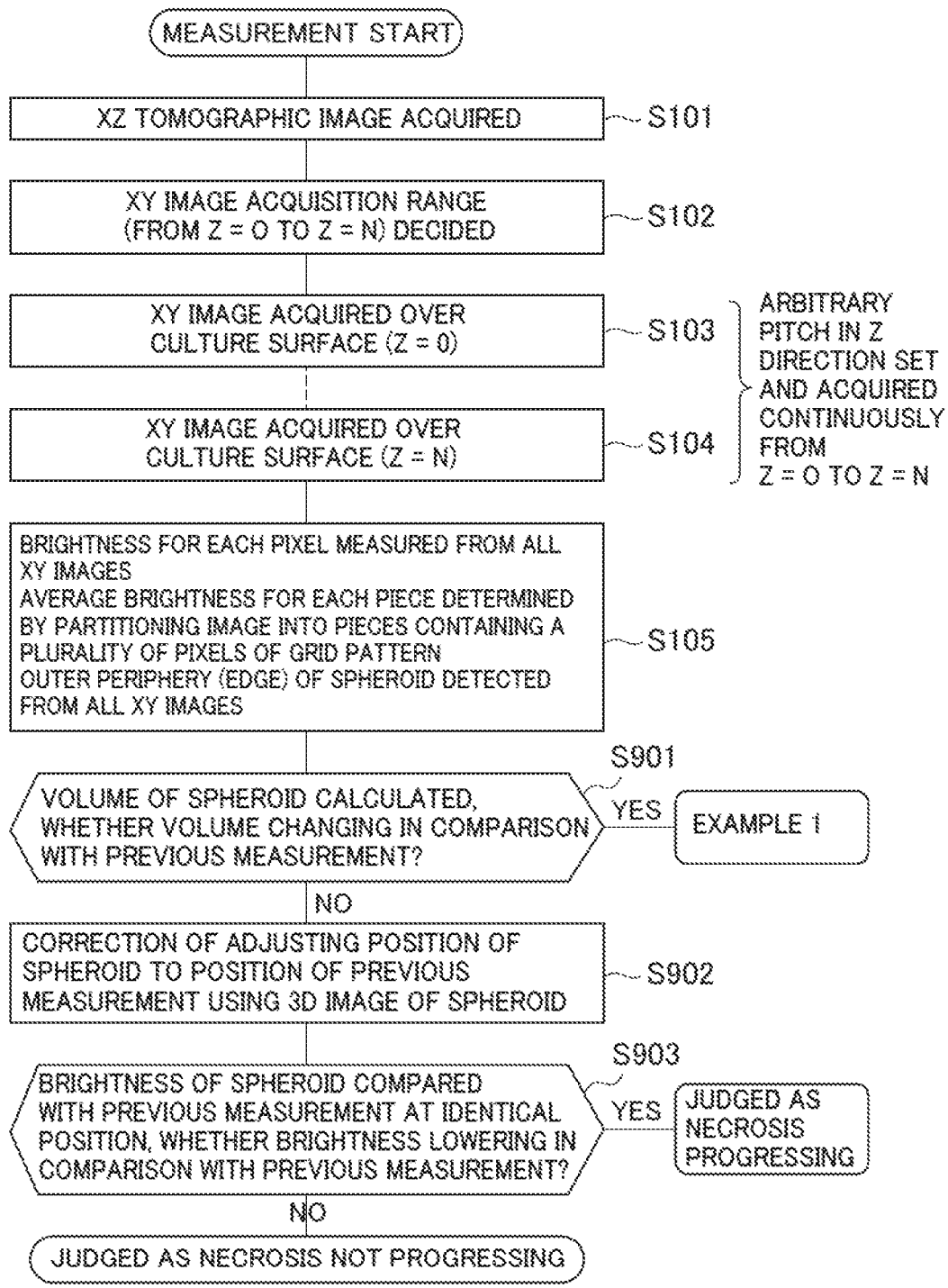
FIG. 9 is a schematic diagram showing another example of an analysis flow of a cell state in a spheroid interior.

A schematic diagram of the flow of measuring a spheroid with an OCT (Optical Coherence Tomograph) and analyzing a cell state in a spheroid interior is shown in FIG. 9. An image of measuring a spheroid is shown in FIG. 5. An image of a perspective view of a spheroid is shown on the left side in FIG. 5. The x, y, and z axes are defined as shown in the figure. Images on xy planes located at different positions on the z axis acquired from the OCT are shown on the right side in FIG. 5. Conceptual images of OCT images relating to FIG. 9 (S105) are shown in FIG. 8.

The flow of measurement and analysis in FIG. 9 is explained mainly. Firstly, XZ tomographic images of a spheroid are acquired at an OCT imaging unit 303 installed in the interior of a thermostatic chamber 302 (S101). The orientations of X, Y, and Z are as shown in FIG. 5, an XY plane is a plane parallel with a culture surface, and the Z axis is the axis perpendicular to the culture surface. The thickness in the Z direction (Z=0 to N) of the spheroid may be clarified from the XZ tomographic images and hence is defined as an XY image acquisition range (S102). Successively, XY images are acquired from Z=0 to Z=N sequentially in XY visual fields (S103 to S104). On this occasion, analysis of a higher degree of accuracy can be obtained as the imaging intervals from Z=0 to Z=N reduce but the intervals can be appropriately set. As a desirable example, the intervals are set so as to be smaller than expected sizes of cells in the Z direction. In acquired XY images, living cells in the spheroid are imaged brightly and, if the region of cell death exists at a part of the spheroid, the region is imaged darkly. Since unevenness of brightness exists even in a relatively narrow region when each of pixels in an actual XY image is examined precisely, an image is partitioned into pieces containing a plurality of pixels of a grid pattern and an average brightness of each of the pieces is determined ((S105) in FIG. 9, (S801) to (S802) in FIG. 8). Further, the outer periphery (edge) of the spheroid is detected by using all the XY images ((S105) in FIG. 9). When the spheroid proliferates to a certain size or larger or the like, the size of the spheroid does not change largely and it is possible to evaluate whether or not necrosis has progressed in the spheroid interior by comparing with data during the previous measurement. On such an occasion, a method of correcting OCT images by the distances travelled by light as shown in Example 1 is not necessarily required. For that reason, when a volume is calculated from a three-dimensional shape of a spheroid (S901) and the volume does not change from the previous measurement, the necrosis state of the spheroid can be judged by the following method. Although a spheroid scarcely moves largely in a culture vessel, correction of adjusting the position of the spheroid to the position during the previous measurement by using a 3D image of the spheroid is implemented in order to compare brightness accurately at an identical position (S902). Then brightness of the spheroid is compared with the previously measured brightness at the identical position and, when the brightness lowers over time, necrosis is judged to have progressed (S903).

The three-dimensional shape and the size of a spheroid, the presence or absence of cell death and the volume of a cell death region in a spheroid interior, and the like, which can be final analysis results, are displayed on a display unit as an output device 307. When the results are displayed in real time, the status of cells can be monitored. Further, remote control is also possible by transmitting to an external device through a network. Otherwise, when the analysis results satisfy a specific condition, an alarm can also be raised by a sound, an image, or the like.

As stated above, according to an embodiment of the present invention, by comparing the measurement results of a spheroid with the previously acquired measurement results of the same spheroid and thus comparing brightness relatively, a cell death part in the spheroid interior can be determined. Further, by displaying the three-dimensional shape and the volume of a spheroid, the presence or absence and the volume of a cell death region in a spheroid interior, and the like on a display device or by storing them in a memory device, information on a cell state in the spheroid can be notified to an operator.

In an automated cell culture apparatus explained in the example of the present invention, it is possible to acquire three-dimensional information of cells non-invasively, and on the basis of the information, feed back warnings or instructions to a device or an operator automatically.

In the present example, a function equivalent to a function configured by software can be implemented also by hardware. Such an embodiment is also included within the scope of the present invention.

The present invention is not limited to the aforementioned embodiments and includes various modified examples. For example, a part of a configuration of an example can be replaced with a configuration of another example and a configuration of an example can be added to a configuration of another example. Further, a part of a configuration of an example can be added to, deleted from, or replaced with another configuration.

LIST OF REFERENCE SIGNS

201: Stem cell
202: Culture surface
301: Automated cell culture apparatus
302: Thermostatic chamber
303: Imaging unit
304: Analysis unit
305: Memory unit
306: Computer
307: Output device
308: Control unit
309: Cell bottle
310: Culture medium bottle
311: Waste fluid bottle
312: Medium flow path
313: Waste flow path
314: Culture vessel
401: Light source
402: Beam splitter
403: Objective lens
404: Reference light mirror
405: Detection system
406: Spheroid
407: Signal light
408: Reference light
409: Coherent light
601: Light source
602: Objective lens
603: Light
604: Z position of measurement point
605: Distance travelled by light in spheroid interior
701: Region of normal living cells
702: Region of cell death

The invention claimed is:

1. A cell analysis method of analyzing a cell death state in the interior of a spheroid, comprising:
   a step of irradiating the spheroid with light;
   a step of acquiring a plurality of spheroid cross-sectional images having different distances from a light irradiation position;
   a step of partitioning each of the images into pieces containing a plurality of pixels of a grid pattern and determining an average brightness for each of the pieces;
   a step of measuring a three-dimensional shape of the spheroid; and
   a step of correcting the average brightness for each of the pieces of the images in consideration of signal strength attenuation depending on the three-dimensional shape of the spheroid, and a distance from the light irradiation position to a measurement position.

2. The cell analysis method according to claim 1, wherein the spheroid is a spheroid formed by agglomerating cells in the vicinity of a culture surface, and a plurality of spheroid cross-sectional images having different distances from the culture surface as the irradiation position are acquired.

3. The cell analysis method according to claim 1, further comprising a step of correcting the spheroid position on the basis of external XYZ coordinates of the spheroid.

4. The cell analysis method according to claim 1, further comprising, after the steps according to claim 1 are implemented:
   a step of irradiating the spheroid with light;
   a step of acquiring a second cross-sectional image of the spheroid; and
   a step of comparing the brightness of the second image with brightness acquired through the steps according to claim 1.

5. A cell analysis apparatus for analyzing a cell death state in the interior of a spheroid, comprising:
   a light source, a light condensation optical system configured to irradiate cells on a culture surface with light from the light source, and a detection optical system configured to detect light from the cells;
   an analysis unit configured to analyze an image based on information acquired from the detection optical system; and
   a measurement unit configured to measure a three-dimensional shape of the spheroid,
   wherein the analysis unit has:
   an image acquisition unit configured to acquire a plurality of cross-sectional images having different distances from the culture surface in the vertical direction;
   a brightness measurement unit configured to measure brightness of the plurality of cross-sectional images; and
   a measurement unit configured to partition each of the images into pieces containing a plurality of pixels of a grid pattern and determine an average brightness for each of the pieces; and
   a state analysis unit configured to correct the average brightness for each of the pieces of the images in consideration of signal strength attenuation depending on the three-dimensional shape of the spheroid, and a distance from the light irradiation position to a measurement position, and analyze a cell death state in the spheroid interior.

6. The cell analysis apparatus according to claim 5, wherein the light source, the light condensation optical system, and the detection optical system are configured as an optical coherence tomograph (OCT).

7. The cell analysis apparatus according to claim 5, further comprising a memory unit configured to store signal strength attenuation data and/or brightness data, which is related to a cell death state in the interior of a spheroid.

8. A cell culture apparatus comprising a culture unit configured to culture a spheroid, an analysis unit configured to analyze a cell death state in the interior of the spheroid by using light, and a control unit configured to control culture and analysis of the spheroid,
   wherein
   (1) the analysis unit has:
   a light source, a light condensation optical system configured to irradiate cells on a culture surface with light from the light source, a detection optical system configured to detect light from the cells;
   an image analysis unit configured to analyze an image based on information acquired from the detection optical system, and
   a measurement unit configured to measure a three-dimensional shape of the spheroid, and
   the image analysis unit has:
   an image acquisition unit configured to acquire a plurality of cross-sectional images having different distances from the culture surface in the vertical direction;

a brightness measurement unit configured to measure brightness of the plurality of cross-sectional images;

a measurement unit configured to partition each of the images into pieces containing a plurality of pixels of a grid pattern and determine an average brightness for each of the pieces; and a state analysis unit configured to correct the average brightness for each of the pieces of the images in consideration of signal strength attenuation depending on the three-dimensional shape of the spheroid, and a distance from the light irradiation position to a measurement position, and analyze a cell death state in the spheroid interior, and (2) the control unit controls at least one of supply of a cell solution, supply of a culture medium, disposal of a culture medium, culture of cells, irradiation of light, detection of light, acquisition of an image, measurement of brightness, and analysis of a cell death state.

9. The cell culture apparatus according to claim 8, wherein the culture unit has:

a thermostatic chamber;

a culture vessel to be arranged in the thermostatic chamber, which is configured to culture a spheroid;

a cell bottle being connected to the culture vessel, which is configured to supply a cell solution;

a culture medium bottle being connected to the culture vessel, which is configured to supply a culture medium; and a waste fluid bottle being connected to the culture vessel, which is configured to store a culture medium discarded from the culture vessel.

10. The cell culture apparatus according to claim 8, wherein the control unit is configured to control the culture of the spheroid in the culture unit on the basis of an output from the state analysis unit.

* * * * *